United States Patent [19]

Hashimoto

[11] Patent Number: 5,508,181
[45] Date of Patent: Apr. 16, 1996

[54] PROCESS FOR PRODUCING ALPHA-HYDROXY ACID OR ALPHA-HYDROXYAMIDE BY MICROORGANISMS

[75] Inventor: Yoshihiro Hashimoto, Kanagawa, Japan

[73] Assignee: Nitto Chemical Industry Co., Ltd., Tokyo, Japan

[21] Appl. No.: 378,006

[22] Filed: Jan. 25, 1995

[30] Foreign Application Priority Data

Jan. 28, 1994 [JP] Japan ................... 6-024888

[51] Int. Cl.⁶ .............. C12P 1/04; C12P 13/02; C12P 7/50; C12P 7/46
[52] U.S. Cl. .............. 435/129; 435/130; 435/139; 435/143; 435/145; 435/146; 435/252.1; 435/822; 435/874; 435/840
[58] Field of Search .................. 435/129, 130, 435/139, 143, 145, 146, 252.1, 82.2, 874, 840

[56] References Cited

U.S. PATENT DOCUMENTS

| | | | |
|---|---|---|---|
| 3,940,316 | 2/1976 | Commeyras et al. | 195/50 |
| 4,001,081 | 1/1977 | Commeyras et al. | 195/29 |
| 5,223,416 | 6/1993 | Endo et al. | 435/128 |
| 5,234,826 | 8/1993 | Yamagami et al. | 435/139 |
| 5,283,193 | 2/1994 | Yamamoto et al. | 435/280 |
| 5,296,373 | 3/1994 | Endo et al. | 435/280 |
| 5,326,702 | 7/1994 | Endo et al. | 435/129 |

FOREIGN PATENT DOCUMENTS

| | | |
|---|---|---|
| 61-56086 | 3/1986 | Japan. |
| 63-222696 | 9/1988 | Japan. |
| 64-10996 | 1/1989 | Japan. |
| 4-440897 | 2/1992 | Japan. |
| 4-40899 | 2/1992 | Japan. |
| 5-219987 | 8/1993 | Japan. |

OTHER PUBLICATIONS

Grant, D. J. W., "Degradative versatility of *Corynebacterium pseudodiphtheriticum* NCIB 10803 which uses amides as carbon source," *Antonie van Leeuwenhoek*, 39 (1973) 273–279.

Okano, V., et al., "Kinetic Secondary Deuterium Isotope Effects for Substituted Benzaldehyde Cyanohydrin Formation," *Journal of the American Chemical Society*, 98:14, 7 Jul. 1976, pp. 4201–4203.

Means, G. E., et al., *Chemical Modification of Proteins*, Holden–Day, San Francisco, 1971, pp. 125–129.

Ogata, Yoshiro, et al., "Equilibrium additions to Carbonyl Compounds," *The Chemistry of the Carbonyl Group*, vol. 2, Edited by Jacob Zabicky, 1970, Interscience publishers, pp. 1–69.

*Primary Examiner*—Herbert J. Lilling
*Attorney, Agent, or Firm*—Sughrue, Mion, Zinn, Macpeak & Seas

[57] ABSTRACT

A process for the production of α-hydroxy acids or α-hydroxyamides in which an α-hydroxynitrile compound or a mixture consisting of an aldehyde and prussic acid, which corresponds to the nitrile compound, is allowed to undergo a microbial reaction to produce the corresponding α-hydroxy acid or α-hydroxyamide, wherein the improvement resides in that phosphite ions or hypophosphite ions are allowed to be present in the reaction system. According to the present invention, since hydrolysis or hydration of nitrile compounds can be carried out by constantly keeping a low concentration level of aldehydes which are considered to be a cause of the enzyme inhibition in the reaction system, the enzyme activity can be maintained stably for a prolonged period of time and the formed acids or amides can therefore be accumulated in a high concentration.

4 Claims, No Drawings

PROCESS FOR PRODUCING ALPHA-HYDROXY ACID OR ALPHA-HYDROXYAMIDE BY MICROORGANISMS

FIELD OF THE INVENTION

This invention relates to a process for the production of α-hydroxy acids or α-hydroxyamides by microorganisms. α-Hydroxy acids or α-hydroxyamides are industrially important for example as materials for the synthesis of various pharmaceuticals and agrochemicals.

BACKGROUND OF THE INVENTION

Examples of known processes for the microbial production of α-hydroxy acids include a process in which glycolic acid, lactic acid, α-hydroxyisobutyric acid and the like are produced from corresponding α-hydroxynitrile compounds by strains belonging to the genusCorynebacterium (cf. JP-A-61-56086; the term "JP-A" as used herein means an "unexamined published Japanese patent application"), a process in which lactic acid, glycolic acid and the like are produced from corresponding α-hydroxynitrile compounds by strains belonging to the genus Bacillus, Bacteridium, Micrococcus or Brevibacterium (cf. U.S. Pat. No. 3,940,316 and JP-B-58-15120; the term "JP-B" as used herein means an "examined Japanese patent publication"), a process in which lactic acid, α-hydroxyisobutyric acid, mandelic acid, α-hydroxybutyric acid, α-hydroxyvaleric acid, α-hydroxy-α-phenyl-propionic acid, α-hydroxy-α-(p-isobutylphenyl)- propionic acid and the like are produced from corresponding α-hydroxynitrile compounds by strains belonging to the genus Pseudomonas, Arthrobacter, Aspergillus, Penicillium, Cochliobolus or Fusarium (cf. JP-A-63-222696), a process in which α-hydroxy-β, β-dimethyl-γ-butyrolactone is produced from a corresponding α-hydroxynitrile compound by strains belonging to the genus Arthrobacter, Aspergillus, Bacillus, Bacteridium, Brevibacterium, Cochliobolus, Corynebacterium, Micrococcus, Nocardia, Penicillium, Pseudomonas or Fusarium (cf. JP-A-64-10996), a process in which mandelonitrile, mandelamide or a substitution product thereof is asymmetrically hydrolyzed by strains belonging to the genus Alcaligenes, Pseudomonas, Rhodopseudomonas, Corynebacterium, Acinetobacter, Bacillus, Mycobacterium, Rhodococcus or Candida (cf. U.S. Pat. No. 5,283,193 and JP-A-2-84198), a process in which α-hydroxyisobutyric acid is produced from α-hydroxyisobutyronitrile by strains belonging to the genus Rhodococcus, Pseudomonas, Arthrobacter or Brevibacterium (cf. JP-A-4-40897), a process in which a predominant amount of R(-)-mandelic acid or a derivative thereof is directly produced from a racemic compound of mandelonitrile or a derivative thereof by strains belonging to the genus Pseudomonas, Alcaligenes, Acinetobacter, Caseobacter, Nocardia, Bacillus, Brevibacterium, Aureobacterium or Rhodococcus (cf. U.S. Pat. No. 5,223,416 and 5,296,373, JP-A4-99495, JP-A-4-99496, JP-A-4-218385 and JP-A-5-95795) and a process in which a predominant amount of D- or L-lactic acid is directly produced from DL-lactonitrile by strains belonging to the genus Enterobacter, Arthrobacter, Caseobacter, Brevibacterium, Aureobacterium, Escherichia, Micrococcus, Streptomyces, Flavobacterium, Aeromonas, Nocardia, Mycoplana, Cellulomonas, Erwina, Candida, Pseudomonas, Rhodococcus, Bacillus, Alcaligenes, Corynebacterium, Microbacterium or Obesumbacterium (cf. U.S. Pat. No. 5,234,826, JP-A-4-99497 and JP-A-5-21987).

Examples of known processes for the microbial production of α-hydroxyamides include a process in which the corresponding amides are produced from lactonitrile, hydroxyacetonitrile, α-hydroxymethylthiobutyronitrile and the like by strains belonging to the genus Bacillus, Bacteridium, Micrciccus or Brevibacterium (cf. U.S. Pat. No. 4,001,081 and JP-B-62-21519) and a process in which α-hydroxy-4-methylthiobutylamide is produced from α-hydroxy-4-methylthiobutyronitrile by strains belonging to the genus Rhodococcus, Corynebacterium, Pseudomonas, Arthrobacter or Alcaligenes (cf. JP-A-4-40899), as well as a report stating that lactamide is accumulated as an intermediate when lactonitrile is hydrolyzed into lactic acid by a strain belonging to the genus Corynebacterium (Grant, D. J. W., Antonievan Leauwenhoek, vol. 39, p. 273, 1973).

However, it is known that α-hydroxynitrile compounds partially dissociate into the corresponding aldehydes and prussic acid in polar solvents, having a certain dissociation constant depending on each compound (cf. V. Okano et al., *J. Am. Chem. Soc.*, vol. 98, p. 4201, (1976)). In addition, since aldehydes generally are able to inactivate enzymes by binding to the protein (cf. *Chemical Modification of Proteins*, G. E. Means et al., Holden-Day, 125, 1971), they cause a problem when an α-hydroxynitrile compound is subjected to enzymatic hydration or hydrolysis, because the aldehyde formed by the dissociation equilibrium inactivates the enzyme within a short period of time, thus making it difficult to obtain α-hydroxy acid or α-hydroxyamide in a high concentration with high productivity.

As a means for overcoming these problems, a process has been proposed in which a sulfite ion, an acid sulfite ion or a dithionite ion is added to a reaction system to effect formation of a reversible complex with the dissociated aldehyde, thereby stabilizing the reaction through sharp reduction of the free aldehyde level in the reaction system (cf. U.S. Pat. No. 5,326,702 and JP-A-5-192189).

However, the dissociation equilibrium constant of complexes with sulfite ions and the like greatly varies depending on the type of aldehyde. Because of this, when an aldehyde which forms a complex having an extremely low dissociation equilibrium constant is used as the target, addition of sulfite ions and the like causes a sharp decrease in the concentration of α-hydroxynitrile in the reaction system to a level lower than the necessary concentration for the enzyme reaction and therefore results in termination of the enzyme reaction. This observation shows that toxicity of all aldehydes cannot easily be reduced by merely adding the aforementioned sulfite ions and the like (*The Chemistry of the Carbonyl Group*, vol. 2, ed. by Jacob Zabicky, 1970, Interscience Publishers).

SUMMARY OF THE INVENTION

As a result of extensive investigation to overcome these problems, the inventors of the present invention have found that the activity and stability of enzymes can be improved greatly in both cases of aldehydes treatable and untreatable with sulfite ions and the like, when ions of phosphite or hypophosphite are present in the reaction solution. The present invention has been accomplished on the basis of this finding.

Accordingly, an object of the present invention is to provide a process for the production of α-hydroxy acids or α-hydroxyamides by microorganisms, in which an α-hydroxynitrile compound represented by the following general formula (1) or a mixture consisting of an aldehyde represented by the following general formula (2) and prussic acid is allowed to undergo a microbial reaction to produce the corresponding α-hydroxy acid or α-hydroxyamide represented by the following general formula (3), wherein the improvement resides in that phosphite or hypophosphite ions are present in the reaction system:

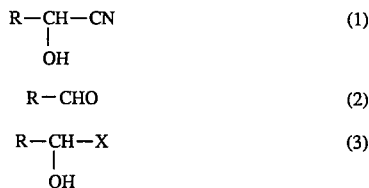

wherein R represents a substituted or unsubstituted alkyl group, a substituted or unsubstituted alkenyl group, a substituted or unsubstituted cycloalkyl group, a substituted or unsubstituted alkoxy group, a substituted or unsubstituted aryl group, a substituted or unsubstituted aryloxy group, or a substituted or unsubstituted, saturated or unsaturated, heterocyclic group and X represents a carboxyl group or an amido group.

Other objects and advantages of the present invention will be made apparent as the description progresses.

DETAILED DESCRIPTION OF THE INVENTION

The phosphite or hypophosphite ions, which can be used in the present invention, are supplied in the form of sodium phosphite, sodium hypophosphite, potassium phosphite, potassium hypophosphite, ammonium phosphite, ammonium hypophosphite or the like, and their action mechanism can be considered as follows.

That is, since the phosphite or hypophosphite ions form complexes with aldehydes similar to the case of sulfite ions and the like, they form complexes quickly with aldehydes released by the dissociation of α-hydroxynitrile compounds in a polar solvent and, as a result, keep the free aldehyde concentration at a low level in the reaction system. On the other hand, complexes of aldehydes with phosphite or hypophosphite ions undergo a nucleophilic reaction by protons or prussic acid, thus re-releasing the corresponding aldehydes or α-hydroxynitrile compounds in a reversible fashion. According to the present invention, since hydration and hydrolysis of nitrile compounds can be carried out while constantly keeping the aldehyde concentration in the reaction system at a low level by the effect of the combination of these functions, the action of aldehydes to inhibit enzyme activities can be reduced to a minimum level and the reaction can be continued stably for a prolonged period of time without causing rapid inactivation of enzymes, thus rendering possible accumulation of the formed acid product in a high concentration. However, it is not clear yet whether or not the enzyme stabilizing mechanism by the phosphite or hypophosphite ions is simply based on the reduction of free aldehyde concentration inside the reaction system.

Since aldehydes generally have a function to inactivate enzyme activities through binding to the protein as described in the foregoing, the effect of the phosphite or hypophosphite ions to prevent inhibition of enzymes seems to be applicable in principle to all aldehyde-related microbial reactions. In other words, according to the process of the present invention for the production of acids or amides from α-hydroxynitrile compounds, the microorganism to be used is not particularly limited, provided that it has a capacity to produce these acids or amides, and the α-hydroxynitrile compound to be used as the substrate is also not particularly limited, provided that it has a capacity to show a dissociation equilibrium with the corresponding aldehyde in the reaction system.

Examples of the microorganisms capable of hydrolyzing α-hydroxynitrile compounds into the corresponding acids include strains belonging to the genera Pseudomonas, Alcaligenes, Acinetobacter, Caseobacter, Corynebacterium, Brevibacterium, Nocardia, Rhodococcus, Gordona, Arthrobacter, Bacillus, Aureobacterium, Enterobacter, Escherichia, Micrococcus, Streptomyces, Flavobacterium, Aeromonas, Mycoplana, Cellulomonas, Erwinia, Candida, Bacteridium, Aspergillus, Penicillium, Cochliobolus, Fusarium and Rhodopseudomonas.

Illustrative examples of these microbial strains include Pseudomonas sp. BC13-2 (FERM BP-3319), sp. BC15-2 (FERM BP-3320), sp. SK13 (FERM BP-3325), sp. SK31 (FERM P11310), SK87 (FERM P-11311) and BC-18 (FERM BP-4536), *Pseudomonas synxanta* IAM 12356, Alcaligenes sp. BC12-2 (FERM P-11263), sp. BC20 (FERM P-11264), sp. BC35-2 (FERM BP-3318) and sp. BC24 (FERM P-12063), Acinetobacter sp. BC9-2 (FERM BP-3317), Caseobacter sp. BC4 (FERM BP-3316) and sp. BC23 (FERM P-11261), *Corynebacterium nitrilophilus* ATCC 21419, *Brevibacterium acetylicum* IAM 1790, *Brevibacterium helvolum* ATCC 11822, Nocardia sp. N-775 (FERM P-4447), *Nocardia asteroides* IFO 3384, *Nocardia calcarea* KCCA 0191, *Nocardia polychromogenes* IFM 19, Rhodococcus sp. SK70 (FERM P-11304), sp. SK92 (FERM BP-3324), sp. HR11 (FERM P-11306) and sp. HT29-7 (FERM BP-3857), *Rhodococcus rhodochrous* ATCC 12674, ATCC 19140 and ATCC 33258, *Rhodococcus erythropolis* IFM 155, IFO 12320, IFO 12538 and IFO 12540, *Gordona terrae* MA-1 (FERM BP-4535), Arthrobacter sp. SK103 (FERM P-11300), sp. HR1 (FERM BP-3323) and sp. HR4 (FERM P-11302), *Arthrobacter oxydans* IFO 12138, *Bacillus subtilis* ATCC 21697, *Bacillus licheniformis* IFO 12197, Bacillus megaterium ATCC 25833, *Aureobacterium testaceum* IAM 1561, Enterobacter sp. SK12 (FERM BP-3322), Escherichia coli IFO 3301, *Micrococcus luteus* ATCC 383, Micrococcus varians IAM 1099, *Micrococcus roseus* IFO 3768, *Streptomyces griseus* IFO 3355, Flavobacterium sp. SK150 (FERM P-11645), *Flavobacterium flavescens* ATCC 8315, *Aeromonas punctata* IFO 13288, *Mycoplana dimorpha* ATCC 4297, *Cellulomonas fimi* IAM 12107, *Erwinia herbicola* IFO 12686 and *Candida guilliermondii* IFO 0566, as well as other strains disclosed in each of the above-cited references as α-hydroxy acid producing microorganisms.

On the other hand, examples of the microorganisms capable of hydrating α-hydroxynitrile compounds into the corresponding amides include strains belonging to the genera Rhodococcus, Corynebacterium, Pseudomonas, Arthrobacter, Alcaligenes, Bacillus, Bacteridium, Micrococcus, Brevibacterium and Nocardia.

Illustrative examples of such microbial strains include Rhodococcus sp. HT40-6 (FERM P-11774), *Rhodococcus rhodochrous* ATCC 33278, *Rhodococcus erythropolis* IFO 12320, *Corynebacterium nitrilophilus* ATCC 21419, Pseudomonas sp. SK87 (FERM P-11311), Arthrobacter sp. HR1 (FERM BP-3323), Alcaligenes sp. BC16-2 (FERM BP-3321), *Brevibacterium acetylicum* IAM 1790 and *Nocardia erythropolis* IFO 12539 and IFO 12540, as well as other strains disclosed in each of the above-cited references as α-hydroxyamide producing microorganisms.

Of these microbial strains, Pseudomonas sp. BC13-2, BC15-2, SK13, SK31, SK87 and BC-18, Alcaligenes sp.

BC12-2, BC20, BC35-2, BC16-2 and BC24, Acinetobacter sp. BC9-2, Caseobacter sp. BC4 and BC23, Nocardia sp. N-775, Rhodococcus sp. SK70, SK92, HR11, HT40-6 and HT29-7, *Gordona terrae* MA-1, Arthrobacter sp. SK103, HR1 and HR4, Enterobacter sp. SK12 and Flavobacterium sp. SK150 have been isolated from natural sources by the present inventors and disclosed in the aforementioned U.S. Pat. Nos. 5,326,702 and 5,223,416, JP-A-5-192189 and JP-A-4-218385, and Japanese Patent Application Nos. 5-246028 and 5-37275 (corresponding EP-A-610,049 and EP-A-610,048, respectively). These strains have been deposited by the present inventors in National Institute of Bioscience and Human Technology, Agency of Industrial Science and Technology, Tsukuba, Japan under the aforementioned respective deposit numbers (FERM Nos.). Their bacteriological properties are as follows.

Other microorganisms described above are well known and can be obtained easily from American Type Culture Collection, Rockville, Md. USA (ATCC), Institute of Applied Microbiology, The University of Tokyo, Tokyo, Japan (IAM), Kaken Pharmaceutical Co., Ltd., Tokyo, Japan (KCC), Institute for Fermentation, Osaka, Japan (IFO) and Eucaryotic Microorganisms Research Center, The University of Chiba, Chiba, Japan (IFM).

[Bacteriological Properties]

Strains BC13-2, BC15-2, SK13, SK31, SK87 and BC-18

| | |
|---|---|
| morphology | rod |
| Gram's stain | − |
| spore | − |
| motility | + |
| flagella | polar |
| oxidase | + |
| catalase | + |
| OF | O |

Strains BC12-2, BC20, BC35-2, BC16-2 and BC24

| | |
|---|---|
| morphology | rod |
| Gram's stain | − |
| spore | − |
| motility | + |
| flagella | peritrichal |
| oxidase | + |
| catalase | + |
| OF | alkalinization |
| formation of 3-ketolactose | − |
| quinones | Q-8 |

Strain BC9-2

| | |
|---|---|
| morphology | rod |
| Gram's stain | − |
| spore | − |
| motility | − |
| oxidase | − |
| catalase | + |
| OF | − |

Strains BC4 and BC23

| | |
|---|---|
| morphology | pleomorphic rod |
| Gram's stain | + |
| spore | − |
| motility | − |
| oxidase | − |
| catalase | + |
| rod-coccus cycle | + |
| cell elongation from colony peripheral | not observed |
| anaerobic growth | − |
| cell wall diamino acid | meso-diaminopimeric acid |
| glycolyl test | − (acetyl type) |

[Bacteriological Properties]

cell wall saccharide composition

| | |
|---|---|
| arabinose | + |
| galactose | + |
| quinones | MK-8 (H$_2$) |

Strains SK70, SK92, HR11 and HT40-6

| | |
|---|---|
| morphology | pleomorphic rod |
| Gram's stain | + |
| spore | − |
| motility | − |
| oxidase | − |
| catalase | + |
| rod-coccus cycle | − |
| cell elongation from colony peripheral | not observed |
| anaerobic growth | − |
| cell wall diamino acid | meso-diaminopimeric acid |
| glycolyl test | + (glycolyl type) | cell wall saccharide composition

| | |
|---|---|
| arabinose | + |
| galactose | + |
| quinones | MK-8 (H$_2$) |

Strain HT29-7

| | |
|---|---|
| morphology | pleomorphic rod |
| Gram's stain | + |
| spore | − |
| motility | − |
| colony color | pink to orange |
| rod-coccus cycle | + |
| cell elongation from colony peripheral | observed |
| formation of aerial hyphae | not observed |
| oxidase | − |
| catalase | + |
| oxygen requirement | aerobic |
| cell wall diamino acid | meso-diaminopimeric acid |
| glycolyl test | + (glycol type) | cell wall saccharide composition

| | |
|---|---|
| arabinose | + |
| galactose | + |
| quinones | MK-9 (H$_2$) |

Strain MA-1

| | |
|---|---|
| morphology | pleomorphic rod |
| Gram's stain | + |
| spore | − |
| motility | − |
| oxidase | − |
| catalase | + |
| colony color | pink to orange |
| rod-coccus cycle | + |
| cell elongation from colony peripheral | observed |
| formation of aerial hyphae | not observed |
| behavior toward oxygen | aerobic |
| cell wall diamino acid | meso-diaminopimeric acid |
| glycolyl test | + (glycolyl type) | cell wall saccharide composition

| | |
|---|---|
| arabinose | + |
| galactose | + |
| quinones | MK-9 (H$_2$) |
| decomposition of adenine | − |
| decomposition of thyrosin | − |
| decomposition of urea | + |
| assimilation of | |
| inositol | − |
| maltose | − |

[Bacteriological Properties]

| | |
|---|---|
| mannitol | + |
| rhamnose | + |
| sorbitol | + |
| sodium m-hydroxy-benzoate | − |
| sodium benzoate | + |
| sodium citrate | + |
| sodium lactate | + |
| testosterone | + |
| acetoamide | − |
| sodium pyruvate | + |
| growth in the presence of 0.02% sodium azide | + |
| growth at 10° C. | + |
| growth at 40° C. | + |
| growth in the presence of 0.001% crystal violet | + |
| growth in the presence of 0.3% phenyl ethanol | + |
| growth in the presence of 5% NaCl | + |
| growth in the presence of 7% NaCl | + |

Strains SK103, HR1 and HR4

| | |
|---|---|
| morphology | pleomorphic rod |
| Gram's stain | + |
| spore | − |
| motility | − |
| oxidase | − |
| catalase | + |
| rod-coccus cycle | + |
| cell elongation from colony peripheral | not observed |
| anaerobic growth | − |
| cell wall diamino acid | lysine |
| glycolyl test | − (acetyl type) |
| cell wall saccharide composition | |
| arabinose | − |
| galactose | − |
| quinones | MK-9 (H$_2$) |

Strain SK12

| | |
|---|---|
| morphology | rod |
| Gram's stain | − |
| spore | − |
| motility | + |
| oxidase | − |
| catalase | + |
| OF | F |
| gas formation from glucose | − |
| formation of indole | − |
| methyl red | + |
| V-P | − |
| utilization of citrate | + |
| formation of hydrogen sulfide | − |
| decomposition of urea | − |
| phenylalanine deamination | + |
| lysine decarboxylation | − |
| arginine dihydrolase | − |
| ornithine decarboxylation | − |

Strain SK150

| | |
|---|---|
| morphology | rod |
| Gram's stain | − |
| spore | − |
| motility | − |
| flagella | − |
| oxidase | + |
| catalase | + |
| OF | O |
| pigment formation | water-insoluble yellow |

The α-hydroxynitrile to be used in the present invention is a compound represented by the aforementioned formula (1) wherein R represents a substituted or unsubstituted alkyl group, a substituted or unsubstituted alkenyl group, a substituted or unsubstituted cycloalkyl group, a substituted or unsubstituted alkoxy group, a substituted or unsubstituted aryl group, a substituted or unsubstituted aryloxy group, or a substituted or unsubstituted, saturated or unsaturated, heterocyclic group, which releases its corresponding aldehyde and prussic acid in a polar solvent such as water, a buffer solution or the like. The thus released aldehyde forms a complex with a phosphite ion or a hypophosphite ion.

Examples of the heterocyclic group include those which contain at least one hetero atom selected from nitrogen, oxygen and sulfur. Examples of the substituent group include an alkyl group, an alkoxy group, an acyl group, an aryl group, an aryloxy group, a halogen atom such as chlorine, bromine or the like, a hydroxy group, an amino group, a nitro group, a thiol group and the like.

Illustrative examples of the α-hydroxynitrile compound include 3-phenyllactonitrile, 3-phenylpropionaldehyde-cyanohydrin, lactonitrile, α-hydroxy-n-propionitrile, α-hydroxy-n-butyronitrile, α-hydroxyisobutyronitrile, α-hydroxy-n-hexyronitrile, α-hydroxy-n-heptyronitrile, α-hydroxy-n-octyronitrile, α,γ-dihydroxy-β,β-dimethylbutyronitrile, acrolein cyanohydrin, methacryl-aldehyde cyanohydrin, 3-chlorolactonitrile, 4-methylthio-α-hydroxybutyronitrile, α-hydroxy-α-phenylpropionitrile and substituted compounds thereof, and illustrative examples of those having aromatic and heterocyclic rings include mandelonitrile, 2-thiophencarboxyaldehyde cyanohydrin, 2-pyridincarboxyaldehyde cyanohydrin, 2-pyrrolcarboxyaldehyde cyanohydrin, 2-furaldehyde cyanohydrin, 2-naphtylaldehyde cyanohydrin and substituted compounds thereof.

In this instance, stereospecific α-hydroxy acids or α-hydroxyamides can be obtained markedly advantageously in comparison with the conventional production processes which require an optical resolution and/or racemization step, when microbial strains capable of producing stereospecific nitrile hydrating or hydrolyzing enzymes are used in the reaction, because such enzymes can easily convert formed α-hydroxy acids or α-hydroxyamides into either form of their optically active substances.

Next, the mode of carrying out the present invention is described.

Hydration or hydrolysis of α-hydroxynitrile compounds is carried out in water or a water-soluble medium such as a buffer solution, by allowing the α-hydroxynitrile compound represented by the aforementioned general formula (1) or a mixture consisting of an aldehyde represented by the aforementioned general formula (2) and prussic acid to contact with cells of a microbial strain or treated cells thereof (disrupted cells, crude or purified enzymes, immobilized cells or enzymes, and the like).

In the reaction solution, a phosphite or a hypophosphite may be used in an amount of generally from about 10 to 1,000 mM, preferably from 50 to 750 mM, more preferably from 50 to 500 mM, when an α-hydroxy acid is produced, or generally from about 250 to 1,000 mM when an α-hydroxyamide is produced.

Concentration of the substrate in the reaction solution may be in the range of generally from about 1 to 100 mM, preferably from 2 to 50 mM, as an α-hydroxynitrile compound, and the amount of a microorganism may be in the range of from about 0.01 to 5.0% (W/V) based on the substrate. The reaction may be carried out at a temperature of generally from about freezing point to 50° C., preferably from 10° to 30° C., for a period of from about 0.1 to 250 hours. In addition, when the solubility of these α-hydroxynitrile compounds in an aqueous medium is extremely small, the reaction may be completed efficiently by the addition of about 0.1 to 5.0% by weight of an appropriate surface active agent such as Triton X-100, Tween 60 or the like, or methanol, ethanol, dimethyl sulfoxide or the like as a mixture solvent, to the reaction solution.

In this manner, amides or acids are converted from the corresponding α-hydroxynitrile compounds and accumulated by the hydrating or hydrolyzing action of microorganisms. Isolation of the product may be effected by removing insoluble substances such as cells and the like from the reaction solution and then subjecting the clear solution to known purification methods such as concentration, ion exchange, chromatography, electrodialysis, extraction, crystallization and the like.

Thus, according to the present invention, since hydration or hydrolysis of nitrile compounds can be carried out by constantly keeping a low concentration level of aldehydes which are considered to be a cause of enzyme inhibition in the reaction system, the enzyme activity can be maintained stably for a prolonged period of time and the formed amides or acids can therefore be accumulated in a high concentration.

The following examples are provided to further illustrate the present invention. It is to be understood, however, that the examples are for purpose of illustration only and are not intended as a definition of the limits of the present invention. All the percents are by weight unless otherwise indicated.

INVENTIVE EXAMPLE 1

Production of 3-phenyllactic acid and 3-phenyllactoamide

Each of Pseudomonas sp. BC-18, Rhodococcus sp. HY29-7, *Gordona terrae* MA-1 and *Brevibacterium acetylicum* IAM 1790 was cultured aerobically at 30° C. for 4 days in the following medium which was supplemented with 0.03% 1-cyclohexynylacetonitrile as an inducing agent.

| Medium composition: | |
| --- | --- |
| glycerol | 20 g |
| yeast extract | 6 g |
| metal mixture* | 5 ml |
| 1 M sodium sulfate | 2 ml |
| 50 mM phosphate buffer (pH 7.5) | 993 ml |

*metal mixture: 8 g of $MgCl_2.6H_2O$, 0.8 g of $CaCl_2$, 0.6 g of $MnSO_4.4H_2O$, 0.12 g of $FeCl_3.6H_2O$ and 0.06 g of $ZnSO_4.7H_2O$ dissolved in 100 ml of distilled water.

Cells were collected from the cultured medium by centrifugation and washed with 50 mM phosphate buffer (pH 8.5). The thus obtained cells were suspended in the above buffer to which was subsequently added a sodium phosphite (sodium is expressed as Na in the following) aqueous solution (pH 8.5) or a Na hypophosphite aqueous solution (pH 8.5) to a final concentration of 50, 100, 250, 500, 750 or 1,000 mM. In this case, the pH value was adjusted with NaOH or HCl. Next, 3-phenyllactonitrile was added to the resulting suspension to a final concentration of 15 mM and the reaction was carried out at 30° C. for 20 hours. As a comparison, the reaction was carried out in the absence of Na phosphite and Na hypophosphite or in the presence of 100 mM Na sulfite. Thereafter, cells were removed from each of the reaction mixtures, and the amounts of 3-phenyllactic acid and 3-phenyllactoamide in the resulting supernatant fluids were measured by HPLC (column, Wakosil ODS 5C18; carrier solution, 0.1M phosphoric acid:acetonitrile=3:1; monitor, 254 nm). The optical purity thereof was determined by HPLC using an optical resolution column (MCI GEL CRS 10W). The results are shown in Table 1.

TABLE 1

| | 3-Phenyllactic acid formed (Mm) | | | 3-Phenyl-lactoamide formed (mM) |
| --- | --- | --- | --- | --- |
| Strain name | BC-18 | HT29-7 | MA-1 | IAM 1790 |
| no addition | 7.69 (79) | 0.46 (45) | 0.45 (45) | 0.17 |
| 100 mM Na sulfite | 8.00 (79) | 0.46 (45) | 0.45 (45) | 0.14 |
| 50 mM Na phosphite | 12.05 (79) | 0.75 (45) | 0.74 (45) | — |
| 100 mM Na phosphite | 14.70 (79) | 0.80 (45) | 0.81 (45) | 0.11 |
| 250 mM Na phosphite | 11.10 (79) | 1.39 (45) | 1.40 (45) | 0.20 |
| 500 mM Na phosphite | 9.98 (79) | 0.97 (45) | 0.98 (45) | 0.42 |
| 750 mM Na phosphite | 8.51 (79) | 0.74 (45) | 0.75 (45) | 1.64 |
| 1000 mM Na phosphite | 8.06 (79) | 1.01 (45) | 1.02 (45) | 2.32 |
| 50 mM Na hypophosphite | 11.10 (79) | 0.85 (45) | 0.86 (45) | — |
| 100 mM Na hypophosphite | 12.70 (79) | 0.90 (45) | 0.92 (45) | 0.12 |
| 250 mM Na hypophosphite | 10.23 (79) | 0.94 (45) | 0.96 (45) | 1.69 |
| 500 mM Na hypophosphite | 10.25 (79) | 0.94 (45) | 0.95 (45) | 1.56 |
| 750 mM Na hypophosphite | 8.63 (79) | 0.83 (45) | 0.82 (45) | 1.84 |
| 1000 mM Na hypophosphite | 8.55 (79) | 0.58 (45) | 0.57 (45) | 1.60 |

( ): Optical Purity (% ee)

INVENTIVE EXAMPLE 2

Production of 4-phenyl-2-hydroxybutyric acid and 4-phenyl-2-hydroxybutylamide

Precipitated cells obtained in the same manner as described in Inventive Example 1 were suspended in the aforementioned buffer to which was subsequently added a Na phosphite aqueous solution (pH 8.5) or a Na hypophosphite aqueous solution (pH 8.5) to a final concentration of 100 or 250 mM. Next, 4-phenylpropionaldehyde cyanohydrin was added to the resulting suspension to a final concentration of 25 mM and the reaction was carried out at 30° C. for 20 hours. As a comparison, the reaction was carried out in the absence of Na phosphite and Na hypophosphite or in the presence of 100 mM Na sulfite. Thereafter, cells were removed from each of the reaction mixtures, and the amounts of 4-phenyl-2-hydroxybutyric acid and 4-phenyl-2-hydroxybutylamide in the resulting supernatant fluids were measured by the same procedure described in Inventive Example 1. The results are shown in Table 2.

TABLE 2

| Strain name | 4-Phenyl-2-hydroxy butyric acid formed (mM) | | 4-Pheny-2-hydroxy butylamide formed (mM) |
| --- | --- | --- | --- |
|  | HT29-7 | MA-1 | IAM 1790 |
| no addition | 15.50 (99) | 15.48 (99) | 0 |
| 100 mM Na sulfite | 17.94 (99) | 17.84 (99) | 1.16 |
| 100 mM Na phosphite | 19.90 (99) | 19.80 (99) | 1.20 |
| 250 mM Na phosphite | 18.27 (99) | 18.28 (99) | 1.90 |
| 100 mM Na hypophosphite | 22.80 (99) | 22.90 (99) | 1.90 |
| 250 mM Na hypophosphite | 20.71 (99) | 20.73 (99) | 1.78 |

( ): Optical Purity (% ee)

INVENTIVE EXAMPLE 3

Production of 3-phenyllactic acid

Cells of strain BC-18 (OD=100) obtained in the same manner as described in Inventive Example 1 were suspended in 50 mM phosphate buffer (pH 8.5) to which was subsequently added a Na phosphite aqueous solution (pH 8.5) to a final concentration of 100 mM. The reaction was carried out in a scale of 100 ml at 30° C. while controlling the pH value at 8.45 to 8.55 using a pH controller. During the reaction, 3-phenyllactonitrile was added in succession to control its concentration at 10 to 20 mM. As a comparison, the reaction was carried out in the absence of Na phosphite or in the presence of 100 mM Na sulfite. After 160 hours of the reaction, amount of the thus formed 3-phenyllactic acid was measured by the same procedure described in Inventive Example 1. The results are shown in Table 3.

TABLE 3

|  | 3-Phenyllactic acid formed (g/l) |
| --- | --- |
| no addition | 15 (79) |
| Na sulfite | 10 (79) |
| Na phosphite | 35 (79) |

( ): Optical Purity (% ee)

INVENTIVE EXAMPLE 4

Production of 4-phenyl-2-hydroxybutyric acid

Cells of strain HT29-7 (OD=16) obtained in the same manner as described in Inventive Example 1 were suspended in 50 mM phosphate buffer (pH 8.5) to which was subsequently added a Na hypophosphite aqueous solution (pH 8.5) to a final concentration of 100 mM. The reaction was carried out at 30° C. in a scale of 30 ml, while adding 3-phenylpropionaldehyde cyanohydrin in succession to control its concentration at 5 to 15 mM. As a comparison, the reaction was carried out in the absence of Na hypophosphite or in the presence of 100 mM Na sulfite. After 95 hours of the reaction, amount of the thus formed 4-phenyl-2-hydroxybutyric acid was measured by the same procedure described in Inventive Example 1. The results are shown in Table 4.

TABLE 4

|  | 4-Phenyl-2-hydroxybutylic acid formed (g/l) |
| --- | --- |
| no addition | 4.5(99) |
| Na sulfite | 14.1(99) |
| Na hypophosphite | 20.0(99) |

( ): Optical Purity (% ee)

INVENTIVE EXAMPLE 5

Production of mandelic acid

Cells of strain MA-1 (OD=6) obtained in the same manner as described in Inventive Example 1 were suspended in 50 mM phosphate buffer (pH 8.2) to which was subsequently added a Na phosphite aqueous solution (pH 8.2) or a Na hypophosphite aqueous solution (pH 8.2) to a final concentration of 100 mM. The reaction was carried out in a scale of 100 ml at 30° C. while controlling the pH value at 8.15 to 8.25 using a pH controller. During the reaction, mandelonitrile was added in succession to control its concentration at 5 to 10 mM. As a comparison, the reaction was carried out in the absence of Na phosphite and Na hypophosphite. After 48 hours of the reaction, amount of the thus formed mandelic acid was measured by the same procedure described in Inventive Example 1. The results are shown in Table 5.

TABLE 5

|  | Mandelic acid formed (g/l) |
| --- | --- |
| no addition | 30 (100) |
| Na phosphite | 100 (100) |
| Na hypophosphite | 120 (100) |

( ): Optical Purity (% ee)

While the invention has been described in detail and with reference to specific examples thereof, it will be apparent to one skilled in the art that various changes and modifications can be made therein without departing from the spirit and scope thereof.

What is claimed is:

1. A process for producing α-hydroxy acids or α-hydroxyamides by microorganisms, in which an α-hydroxynitrile compound represented by the following general formula (1) or a mixture consisting of an aldehyde represented by the following general formula (2) and prussic acid is allowed to undergo a microbial reaction to produce the corresponding α-hydroxy acid or α-hydroxyamide represented by the following general formula (3), wherein the improvement resides in that phosphite ions or hypophosphite ions are allowed to be present in the reaction system:

-continued

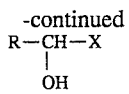
(3)

wherein R represents a substituted or unsubstituted alkyl group, a substituted or unsubstituted alkenyl group, a substituted or unsubstituted cycloalkyl group, a substituted or unsubstituted alkoxy group, a substituted or unsubstituted aryl group, a substituted or unsubstituted aryloxy group, or a substituted or unsubstituted, saturated or unsaturated heterocyclic group, and X represents a carboxyl group or an amido group.

2. The process according to claim 1, wherein said α-hydroxy acid or α-hydroxyamide represented by the general formula (3) is an optically active substance.

3. The process according to claim 1, wherein said phosphite or hypophosphite ions are sodium phosphite, sodium hypophosphite, potassium phosphite, potassium hypophosphite, ammonium phosphite or ammonium hypophosphite.

4. The process according to claim 1, wherein said phosphite or hypophosphite is used in an amount of from about 10 to 1,000 mM.

* * * * *